United States Patent
Brasington et al.

(10) Patent No.: US 7,655,021 B2
(45) Date of Patent: Feb. 2, 2010

(54) DILATOR WITH EXPANDABLE MEMBER

(75) Inventors: Evan Brasington, Duxbury, MA (US); Michael Madden, Princeton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 451 days.

(21) Appl. No.: 10/385,208

(22) Filed: Mar. 10, 2003

(65) Prior Publication Data
US 2004/0181273 A1 Sep. 16, 2004

(51) Int. Cl.
*A61M 29/02* (2006.01)
(52) U.S. Cl. ...................................... 606/192
(58) Field of Classification Search ......... 606/190–199; 604/161, 164.1, 164.01, 164.11, 165.01, 604/165.02, 165.04; 600/184; 24/615, 644–648, 24/614; 403/326, 329; 285/116
See application file for complete search history.

(56) References Cited

U.S. PATENT DOCUMENTS

| | | | |
|---|---|---|---|
| 2,548,602 A | | 4/1951 | Greenburg |
| 2,799,273 A | | 7/1957 | Oddo |
| 4,013,080 A | * | 3/1977 | Froning .................. 604/165.01 |
| 4,295,464 A | | 10/1981 | Shihata |
| 4,327,709 A | | 5/1982 | Hanson et al. |
| 4,469,100 A | | 9/1984 | Hardwick |
| 4,569,106 A | * | 2/1986 | Lovato .................. 24/615 |
| 4,610,674 A | * | 9/1986 | Suzuki et al. ............. 604/528 |
| 4,688,337 A | * | 8/1987 | Dillner et al. .............. 24/616 |
| 4,840,613 A | * | 6/1989 | Balbierz ................ 604/533 |
| 4,930,496 A | | 6/1990 | Bosley, Jr. |
| 4,932,956 A | | 6/1990 | Reddy et al. |
| 4,995,878 A | | 2/1991 | Rai |
| 5,064,414 A | * | 11/1991 | Revane ................. 604/165.01 |
| 5,092,846 A | * | 3/1992 | Nishijima et al. ...... 604/167.04 |
| 5,098,392 A | * | 3/1992 | Fleischhacker et al. 604/164.05 |
| 5,098,393 A | * | 3/1992 | Amplatz et al. ........ 604/167.03 |
| 5,183,464 A | | 2/1993 | Dubrul et al. |
| 5,188,630 A | | 2/1993 | Christoudias |
| 5,380,304 A | | 1/1995 | Parker |
| 5,391,152 A | * | 2/1995 | Patterson ............... 604/165.04 |
| 5,423,755 A | | 6/1995 | Kesten et al. |
| 5,454,790 A | | 10/1995 | Dubrul |

(Continued)

FOREIGN PATENT DOCUMENTS

EP  0 537 895 B1  10/1992

(Continued)

OTHER PUBLICATIONS

'Applied Access Sheath' [online]. Applied Medical. [Retrieved on Jan. 28, 2003]. Retrieved from the Internet: <URL http://www.appliedmed.com/BROCHURES/UROLOGY/Accesssheath.SS.Mech2.pdf>.

(Continued)

*Primary Examiner*—Anhtuan T Nguyen
*Assistant Examiner*—Elizabeth Houston

(57) ABSTRACT

The invention relates to a dilator having an expandable member and relates to a dilator and access sheath assembly including a first conduit which includes a wall defining a lumen therethrough and which is sufficiently rigid to dilate tissue in a body vessel; a member coaxially surrounding a first section of the first conduit, where the member is capable of expanding; and a second conduit coaxially surrounding a second section of the first conduit.

29 Claims, 11 Drawing Sheets

U.S. PATENT DOCUMENTS

| | | | | |
|---|---|---|---|---|
| 5,471,716 | A | * | 12/1995 | Takahashi .................... 24/615 |
| 5,549,635 | A | | 8/1996 | Solar |
| 5,571,091 | A | * | 11/1996 | Davis et al. ............ 604/164.11 |
| 5,653,230 | A | * | 8/1997 | Ciaglia et al. .......... 128/207.15 |
| 5,676,688 | A | | 10/1997 | Jaker et al. |
| 5,700,253 | A | | 12/1997 | Parker |
| 5,722,983 | A | * | 3/1998 | Van Der Weegen ......... 606/193 |
| 5,779,670 | A | | 7/1998 | Bidwell et al. |
| 5,816,622 | A | * | 10/1998 | Carter ......................... 285/45 |
| 5,836,951 | A | | 11/1998 | Rosenbluth et al. |
| 5,843,161 | A | | 12/1998 | Solovay |
| 5,846,251 | A | | 12/1998 | Hart |
| 5,911,702 | A | | 6/1999 | Romley et al. |
| 5,935,122 | A | | 8/1999 | Fourkas et al. |
| 5,971,958 | A | * | 10/1999 | Zhang ................... 604/165.02 |
| 5,972,015 | A | | 10/1999 | Schribner et al. |
| 5,989,276 | A | * | 11/1999 | Houser et al. ............... 606/170 |
| 6,004,328 | A | | 12/1999 | Solar |
| 6,022,319 | A | | 2/2000 | Willard et al. |
| 6,056,762 | A | * | 5/2000 | Nash et al. .................. 606/153 |
| 6,066,100 | A | * | 5/2000 | Willard et al. ............... 600/452 |
| 6,080,174 | A | | 6/2000 | Dubrul et al. |
| 6,093,173 | A | * | 7/2000 | Balceta et al. .......... 604/164.01 |
| 6,120,480 | A | * | 9/2000 | Zhang et al. ........... 604/164.01 |
| 6,143,014 | A | | 11/2000 | Dehdashtian et al. |
| 6,203,488 | B1 | | 3/2001 | Kulisz et al. |
| 6,240,968 | B1 | | 6/2001 | Bigonzi-Jaker et al. |
| 6,273,895 | B1 | * | 8/2001 | Pinchuk et al. ............. 606/108 |
| 6,336,914 | B1 | * | 1/2002 | Gillespie, III .......... 604/165.01 |
| 6,447,540 | B1 | | 9/2002 | Fontaine et al. |
| 6,471,684 | B2 | | 10/2002 | Dulak et al. |
| 6,494,860 | B2 | | 12/2002 | Rocamora et al. |
| 6,547,776 | B1 | * | 4/2003 | Gaiser et al. ................ 604/506 |
| 6,692,484 | B1 | * | 2/2004 | Karpiel et al. .............. 604/544 |
| 6,698,966 | B2 | * | 3/2004 | Hilton et al. ................ 403/321 |
| 6,719,772 | B2 | * | 4/2004 | Trask et al. ................. 606/191 |
| 6,796,991 | B2 | * | 9/2004 | Nardeo ....................... 606/191 |
| 6,808,520 | B1 | | 10/2004 | Fourkas et al. |
| 7,011,342 | B2 | * | 3/2006 | Guivarc'h et al. ........... 285/116 |
| 2001/0012950 | A1 | | 8/2001 | Nishtala et al. |
| 2001/0044624 | A1 | | 11/2001 | Seraj et al. |
| 2002/0007206 | A1 | | 1/2002 | Bui et al. |
| 2002/0032406 | A1 | | 3/2002 | Kusleika |
| 2002/0091405 | A1 | | 7/2002 | Kieturakis et al. |
| 2003/0045834 | A1 | * | 3/2003 | Wing et al. .................. 604/161 |
| 2004/0006344 | A1 | | 1/2004 | Nguyen et al. |
| 2004/0055122 | A1 | * | 3/2004 | Matoba ....................... 24/615 |

FOREIGN PATENT DOCUMENTS

| | | |
|---|---|---|
| EP | 0 530 970 B1 | 1/1996 |
| EP | 0 617 977 B1 | 7/1998 |
| EP | 0 931 558 B1 | 10/2003 |
| WO | WO 98/00191 | 1/1998 |
| WO | WO 99/16499 | 4/1999 |
| WO | WO 99/64101 A1 | 12/1999 |
| WO | WO 02/35134 | * 5/2002 |

OTHER PUBLICATIONS

'UroMax Ultra High Pressure Balloon Catheter' [online]. Boston Scientific Corporation. [Retrieved on Jan. 28, 2003]. Retrieved from the Internet: <URL: http://www.bostonscientific.com/med_specialty/deviceDetail.jhtml?task=tskBasicDevice.jhtml&sectionId=4&relId=8,386,387,388&deviceId=35&uniqueId=MPDB203>.

Boston Scientific Corporation, "Navigator™ Ureteral Access Sheath Set with Hydrophilic Coating," 2002, 4 pages.

'Urological Surgery' [online]. NYU Medical Center. [Retrieved on Jan. 25, 2003]. Retrieved from the Internet: <URL: http://mininvasive.med.nyu.edu.urology/ureteroscopy.html>.

Fernando et al. (2000), "Technique of Endopyelotomy with the Acucise Cutting Balloon," *Brazilian Journal of Urology*, 26:71-75.

Joshi, R. Ureteroscopy [online]. [Retrieved on Jan. 25, 2003]. Retrieved from the Internet: <URL: http://www.bhj.org/journal/1999_4103_july99/sp_451.htm>.

'Pursuit' [online]. Cook Urological Incorporated. Retrieved on Jan. 13, 2003]. Retrieved from the Internet: <URL: http://www.cookurological.com/html_pages/pursuitballoon.html>.

'Pursuit Ureteral Dilation Balloon Catheters' [online]. Cook Urological Incorporated. [Retrieved on Jan. 13, 2003]. Retrieved from the Internet: <URL: http://www.cookurological.com/pdf/PABD699.pdf>.

'Omega NV Balloon Ureteral Dilator Sets' [online]. Cook Urological Incorporated. [Retrieved on Jan. 13, 2003]. Retrieved from the Internet: <URL: http://www.cookurological.com/pdf/perc.pdf>. page 36.

Boston Scientific Corporation, "Navigator™ Ureteral Access Sheath Set with Uro-Glide™ Coating," Nov. 2002, 20 pages.

* cited by examiner

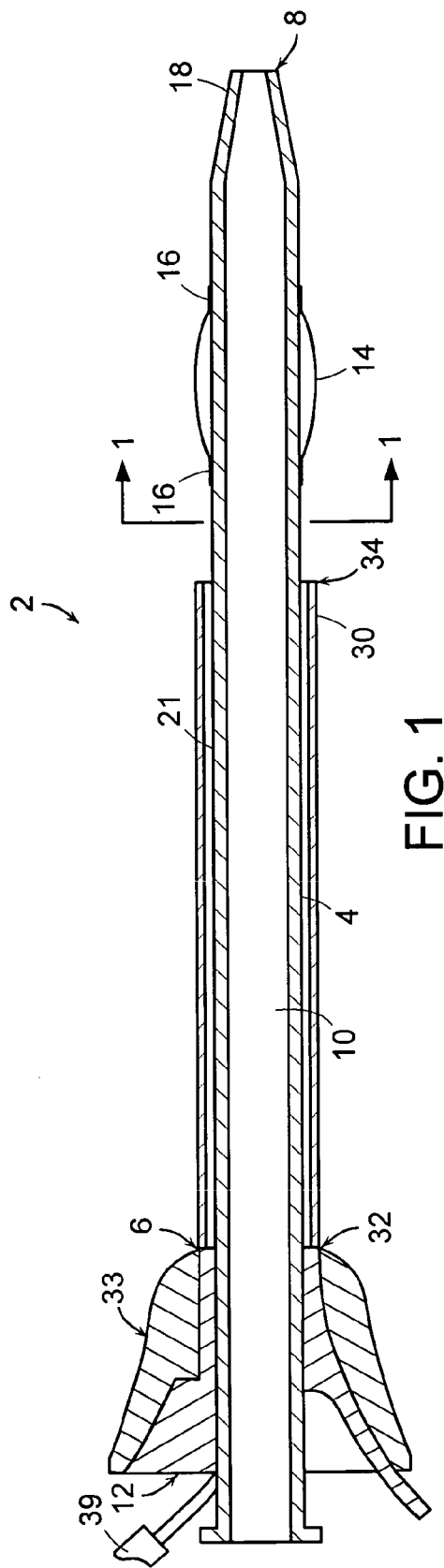
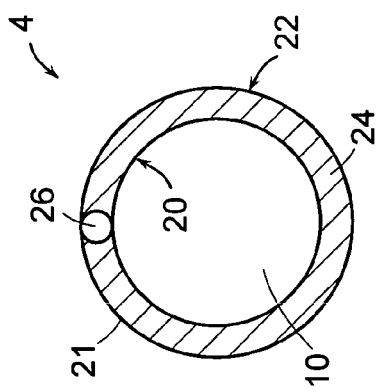

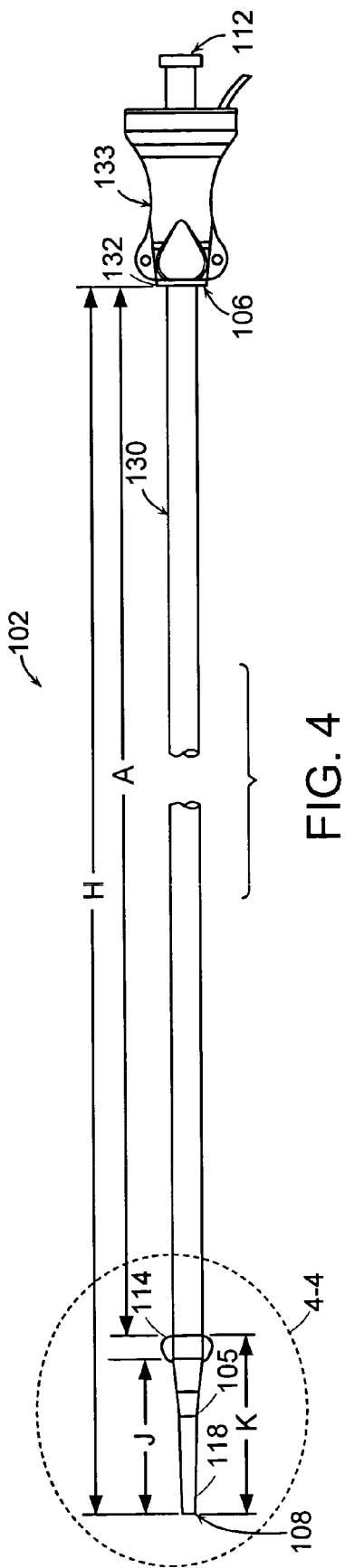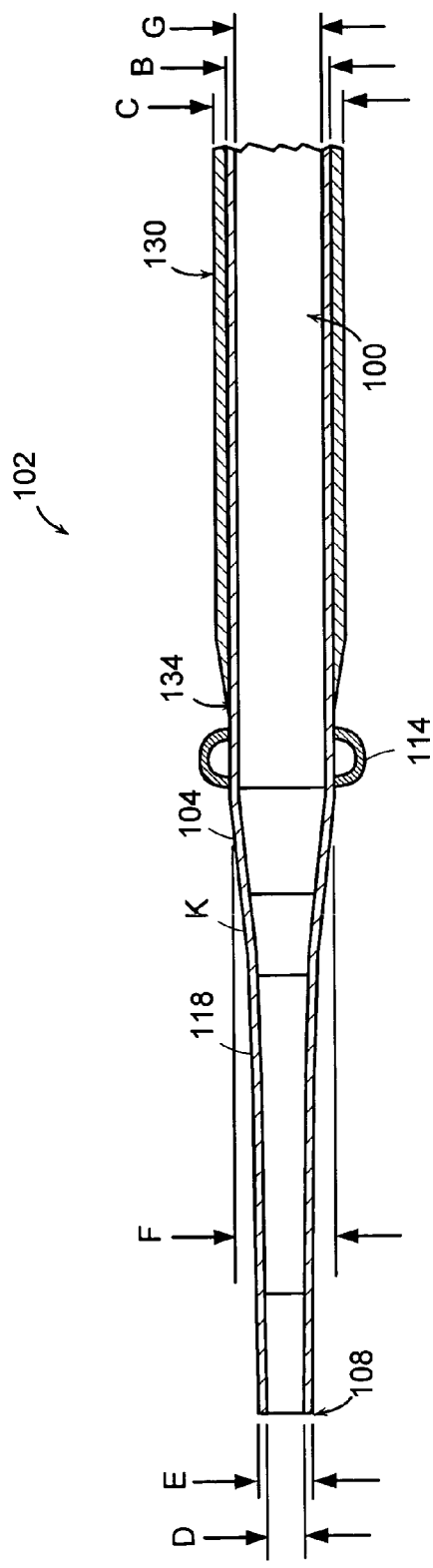

| ROW | FRENCH SIZE | "A" (CM) SHEATH WORKING LENGTH ±4.4 MM (.18") | "B" SHEATH TIP I.D. REF (INCHES) | "C" SHEATH O.D. ±.005 (INCHES) | "D" DILATOR TIP I.D. ±.003 (INCHES) | "E" DILATOR TIP O.D. ±.003 (INCHES) | "F" DILATOR BODY O.D. ±.003 (INCHES) | "G" DILATOR BODY I.D. ±.003 (INCHES) | "H" (CM) DILATOR WORKING LENGTH ±1.65 MM (.065") | "J" (CM) DILATOR TAPERED LENGTH ±0.1 CM (.039") | "K" (CM) EXPOSED TIP LENGTH (REF) |
|---|---|---|---|---|---|---|---|---|---|---|---|
| 1 | 11/13 | 27.80 (10.94") | .139 | .172 | .042 | .066 | .142 | .098 | 30.62 (12.055") | 1.92 (.755") | 2.83 |
| 2 | 11/13 | 35.80 (14.09") | .139 | .172 | .042 | .066 | .142 | .098 | 38.62 (15.206") | 1.92 (.755") | 2.83 |
| 3 | 11/13 | 45.80 (18.03") | .139 | .172 | .042 | .066 | .142 | .098 | 48.63 (19.146") | 1.92 (.755") | 2.83 |
| 4 | 13/15 | 27.80 (10.94") | .167 | .200 | .042 | .066 | .170 | .122 | 30.98 (12.198") | 2.27 (.895") | 3.20 |
| 5 | 13/15 | 35.80 (14.09") | .167 | .200 | .042 | .066 | .170 | .122 | 38.98 (15.348") | 2.27 (.895") | 3.20 |
| 6 | 13/15 | 45.80 (18.03") | .167 | .200 | .042 | .066 | .170 | .122 | 48.99 (19.288") | 2.27 (.895") | 3.20 |

FIG.16

| 11/13 FR. | DESCRIPTION DILATOR O.D.: 0.142" | | |
| --- | --- | --- | --- |
| SAMPLE # | 0.098" I.D. | 0.082" I.D. | 0.060" I.D. |
| 1 | 1.39 | 1.62 | 1.75 |
| 2 | 1.25 | 1.62 | 1.63 |
| 3 | 1.61 | 1.66 | 1.73 |
| 4 | 1.57 | 1.61 | 1.69 |
| 5 | 1.47 | 1.62 | 1.73 |
| 6 | 1.67 | 1.62 | 1.69 |
| AVERAGE | 1.49 | 1.63 | 1.70 |
| MIN. | 1.25 | 1.61 | 1.63 |
| MAX. | 1.67 | 1.66 | 1.75 |

FIG. 17

| 13/15 FR. | DESCRIPTION: DILATOR O.D.: 0.172" | | |
| --- | --- | --- | --- |
| SAMPLE # | 0.122: I.D. | 0.090" I.D. | 0.110" I.D. |
| 1 | 1.60 | 2.02 | 1.80 |
| 2 | 1.75 | 2.02 | 1.86 |
| 3 | 1.75 | 2.00 | 1.88 |
| 4 | 1.83 | 2.05 | 1.76 |
| 5 | 1.81 | 2.02 | 1.69 |
| 6 | 1.61 | 1.96 | 1.80 |
| AVERAGE | 1.73 | 2.01 | 1.80 |
| MIN. | 1.60 | 1.96 | 1.69 |
| MAX. | 1.83 | 2.05 | 1.88 |

FIG. 18

DILATOR WITH EXPANDABLE MEMBER

FIELD OF THE INVENTION

The invention generally relates to dilators having an expandable member. More particularly, the invention relates to a dilator having an expandable balloon at one end for use in association with a sheath.

BACKGROUND OF THE INVENTION

Ureteroscopy is a procedure that can be used when ureteral stones, strictures, or tumors are present. Ureteral stones are generally formed in the kidney and pass down into the ureter where they become lodged. In the ureter, stones block the passage of urine to the bladder, generating pain for a patient. Often, infection ensues, and in certain cases the infection can be life threatening. Ureteroscopy enables a surgeon to access, disintegrate, and remove ureteral stones.

Strictures are a constriction of the ureter associated with abnormal tissue. A stricture can result for various reasons, including congenital abnormalities, previous surgery, passage of stones, or radiation therapy. Ureteroscopy allows a surgeon to locate and repair a stricture using tools, such as expandable balloons and lasers.

Ureteroscopy also can be used when tumors are present in the ureter. Using ureteroscopy, surgeons can better diagnose the cancer by taking tissue samples. In some cases, the cancer can be treated through the use of an ureteroscopy procedure, thereby avoiding the use of more invasive techniques. Accordingly, devices and related methods are needed to allow a medical professional to undertake such procedures.

SUMMARY OF THE INVENTION

The present invention relates to a dilator having an expandable member. The dilator is a multifunctional device as it can dilate tissue as a dilator and expand tissue as an expandable member. The dilator can be connected to an access sheath. Such devices are useful in ureteroscopy procedures. The device, however, can be used in any procedure where it is required to access and dilate any vessel, lumen, or other orifice in the body, or to bypass various types of blockages formed thereby or occurring therein.

In an ureteroscopy procedure utilizing devices according to the invention, a medical professional inserts a guide wire through the urethra, into the bladder, through the ureteral orifice, into the ureter, and then to the kidney. Following placement of the guide wire, the medical professional slides an assembly of the access sheath and the dilator with an expandable member over the guide wire. When a blockage of the urinary tract is encountered as, for example, but without limitation, when a constriction of the ureteral orifice, a stricture, a stone, or a tumor is encountered, the medical professional can expand the expandable member on the dilator to relieve or bypass the blockage. Once the blockage has been relieved or bypassed, the medical professional can deflate the expandable member. The expandable member, because it is connected to the dilator, remains immediately available to the medical professional while the dilator remains in the lumen of the access sheath.

Devices and methods according to the invention aid surgery because a medical professional does not have to remove the dilator according to the invention from within the access sheath, or remove the entire balloon dilator access sheath assembly according to the invention, before inserting a separate expandable member into the access sheath, or into the body vessel if the sheath is removed as well, to solve a blockage problem. This reduces the time of surgeries to the benefit of the patient and simplifies the surgical procedure to the benefit of the medical professional by decreasing the number of interventions that need to be undertaken to pass tools. Costs are also reduced, because the use of separate dilators and balloon catheters may be avoided.

One aspect of the invention relates to a dilator and access sheath assembly. The dilator and access sheath assembly includes a first conduit where the conduit is sufficiently rigid to dilate tissue in a body vessel. The assembly also can include a member coaxially surrounding a first section of the first conduit, where the member is capable of expanding, and can include a second conduit coaxially surrounding a second section of the first conduit.

The assembly described above can have any of the following features or characteristics. The first section can overlap the second section. Alternatively, the first and second sections can be distinct and not overlap. The first conduit can include a tapered tip. The member can include a balloon, and the balloon can be compliant or non-complaint. The assembly also can include a first hub adjacent to the first conduit and a second hub adjacent to the second conduit, where the first and second hubs are connectable. The first conduit also can include a wall defining a lumen therethrough. A passage can extend within the wall and along at least a portion of the first conduit, the passage communicating with the member. The first conduit can define two or more lumens. The assembly can also include a passage that extends along at least a portion of the first conduit, where the passage communicates with the member, and the passage can extend within the wall of the first conduit.

Another aspect of the invention relates to a method for accessing a surgical site. The method includes inserting a dilator and access sheath assembly into a patient, the assembly including a first conduit, a member coaxially surrounding a first section of the first conduit and capable of expansion, and a second conduit coaxially surrounding a second section of the first conduit. The method also includes advancing the assembly through a body vessel to dilate the tissue of the vessel and, without the removal of the assembly from the vessel, expanding the member to alleviate a blockage in the vessel.

The method described above can have any of the following features or characteristics. The first section can overlap the second section. Alternatively, the first and second sections can be distinct and not overlap. The first conduit can include a tapered tip. The member can be a balloon. The method also can include the further steps of unexpanding the member and advancing the assembly beyond the blockage. The blockages can include, without limitation, a constriction of the ureteral orifice, a sphincter, a stone, and a tumor.

BRIEF DESCRIPTION OF THE DRAWINGS

The foregoing and other objects, aspects, and advantages of the invention and the various features thereof may be more fully understood from the following description when read together with the accompanying drawings. In the drawings, like reference characters generally refer to the same parts throughout the different views. Also, the drawings are not necessarily to scale, emphasis instead generally being placed upon illustrating the principles of the technology.

FIG. 1 depicts a schematic side section view of one embodiment of a balloon dilator access sheath assembly.

FIG. 2 depicts a schematic cross section of the balloon dilator access sheath assembly of FIG. 1 taken along line 1-1 of FIG. 1.

FIG. 4 depicts a schematic side view of a second embodiment of a balloon dilator access sheath assembly.

FIG. 5 depicts a schematic side section view of an enlarged portion 4-4 of the assembly of FIG. 4, as shown in FIG. 4.

FIG. 16 depicts various size configurations for the second embodiment of the balloon dilator access sheath assembly.

FIG. 17 depicts the results of a three point bend stiffness test conducted on balloon dilator access sheath assemblies of the present invention.

FIG. 18 depicts the results of a three point bend stiffness test conducted on balloon dilator access sheath assemblies of the present invention.

DETAILED DESCRIPTION OF THE INVENTION

Figure 3:
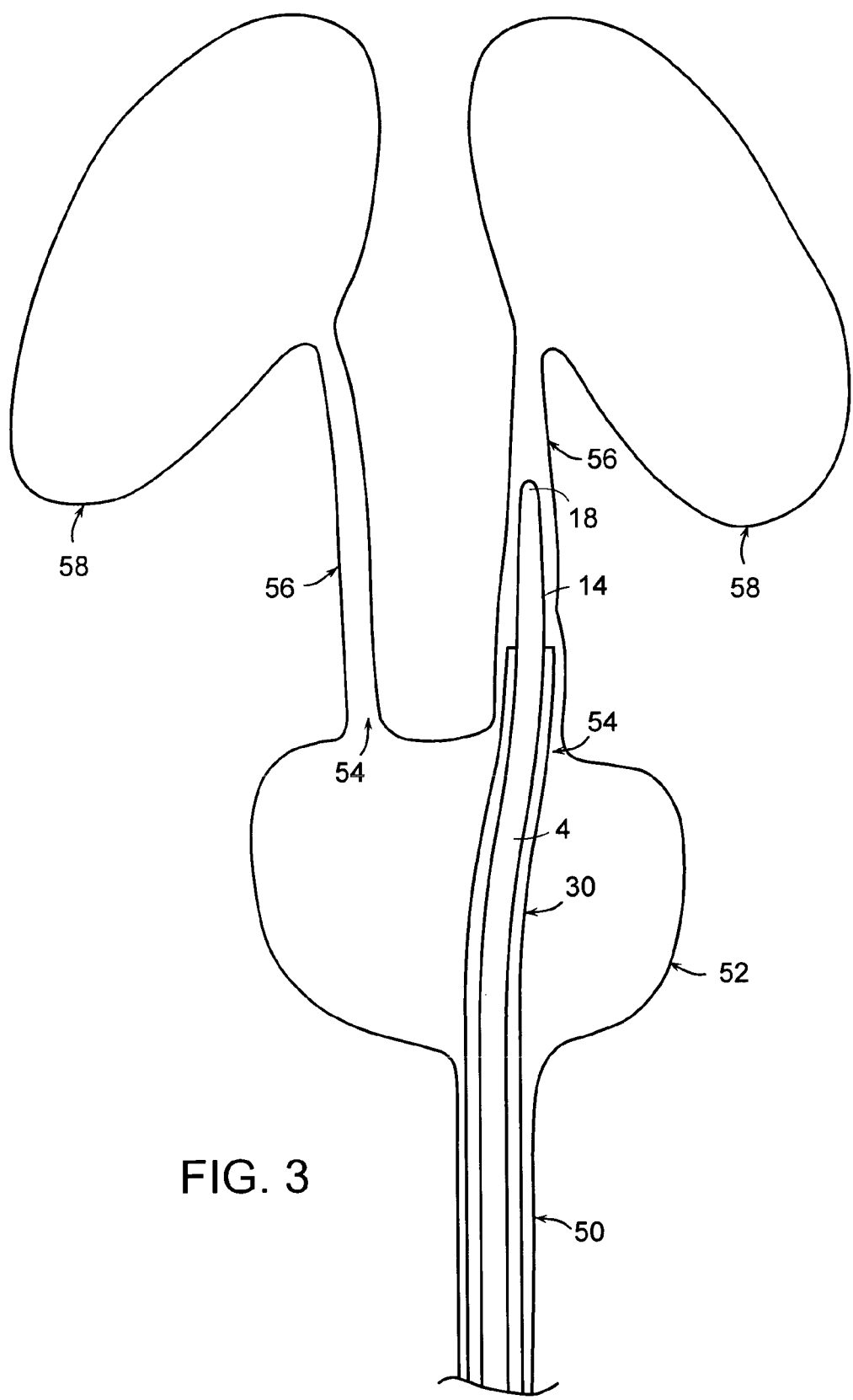
FIG. 3 schematically depicts the balloon dilator access sheath assembly of FIG. 1 in use during a ureteroscopy procedure.
Figure 6:
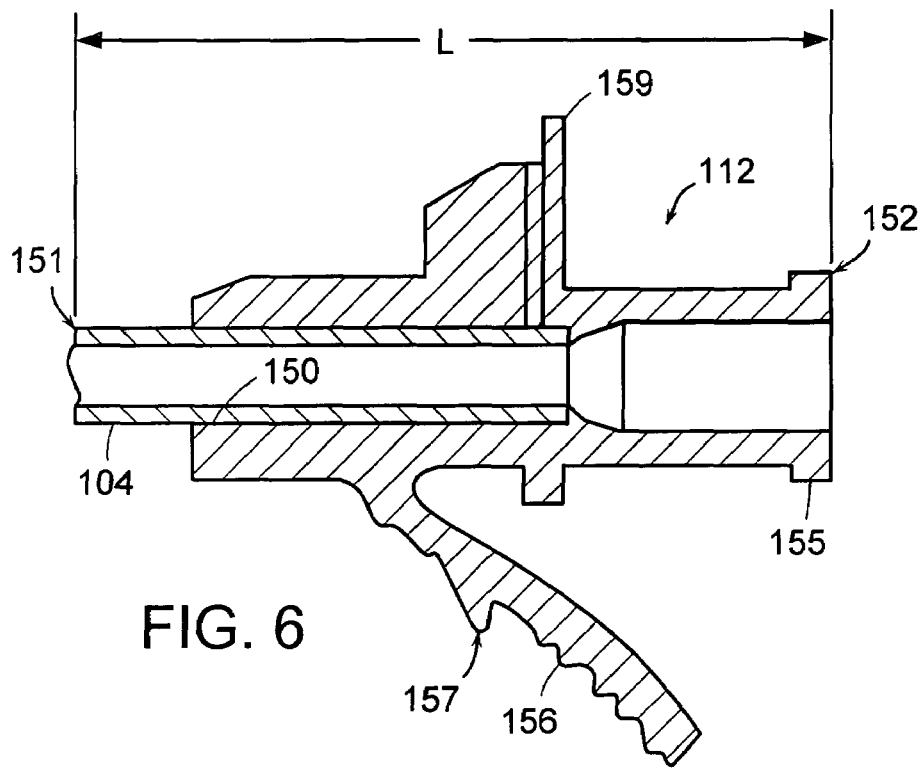
FIG. 6 depicts a schematic side section view of a dilator hub of the balloon dilator access sheath assembly of FIG. 4.
Figure 7:
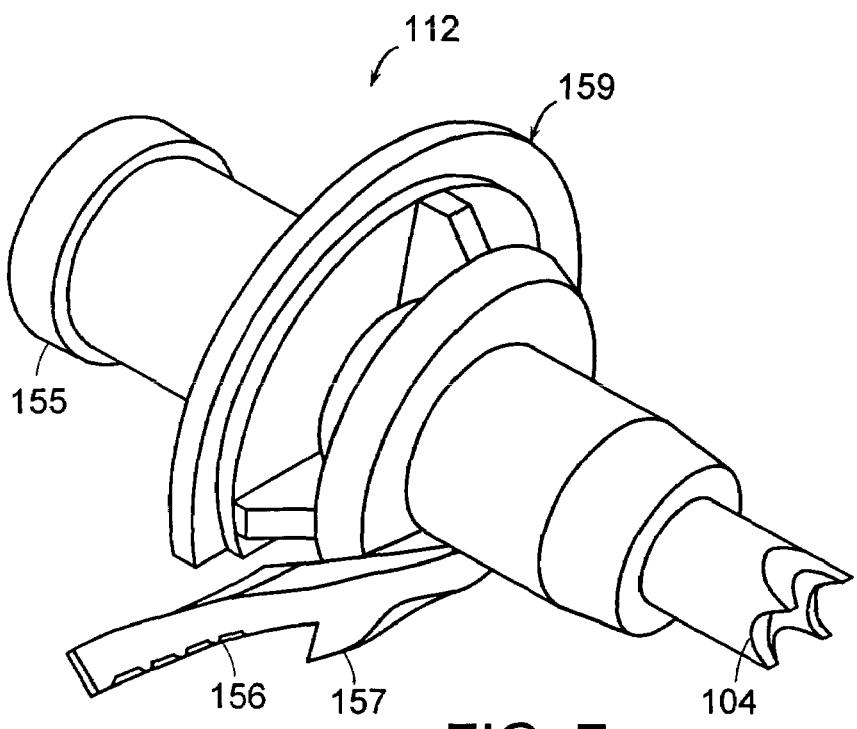
FIG. 7 depicts a schematic perspective view of the dilator hub of the balloon dilator access sheath assembly of FIG. 4.
Figure 8:
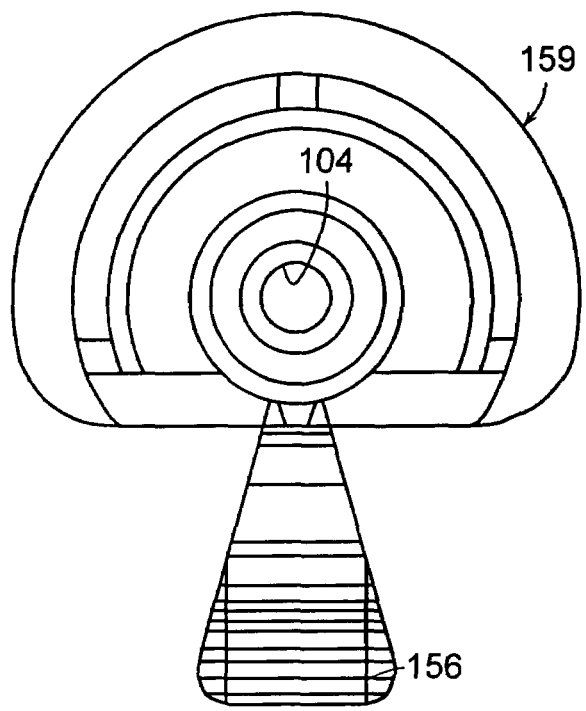
FIG. 8 depicts a schematic distal end view of the dilator hub of the balloon dilator access sheath assembly of FIG. 4.
Figure 9:
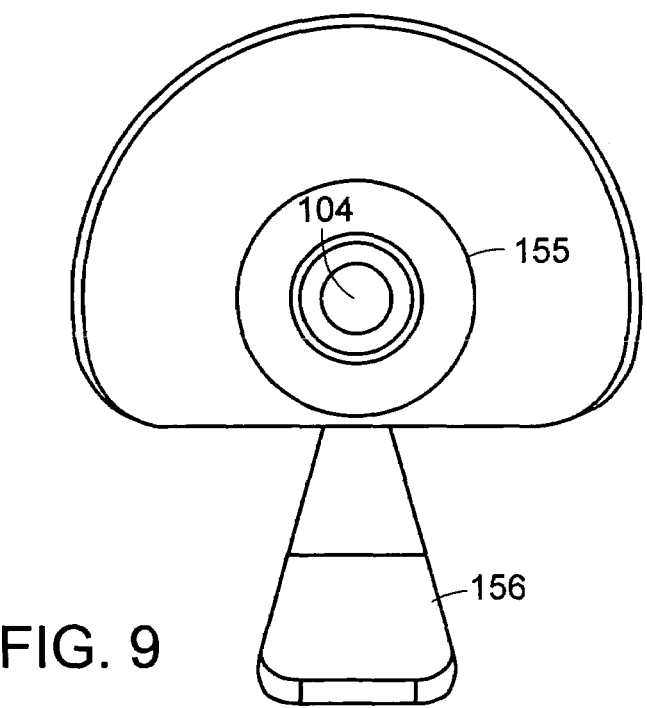
FIG. 9 depicts a schematic proximal end view of the dilator hub of the balloon dilator access sheath assembly of FIG. 4.
Figure 11:
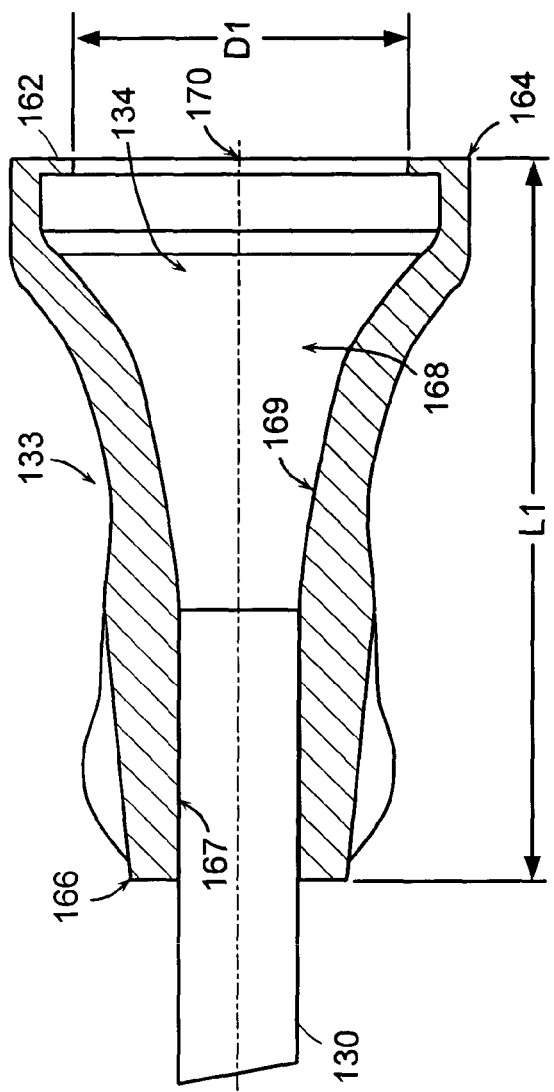
FIG. 11 depicts a schematic cross section view of the access sheath hub of FIG. 10 taken along line 10-10 of FIG. 10.
Figure 10:
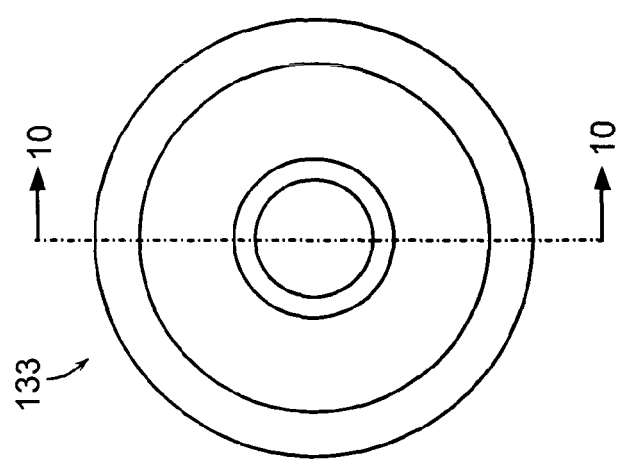
FIG. 10 depicts a schematic top view of an access sheath hub of the balloon dilator access sheath assembly of FIG. 4.
Figure 12:
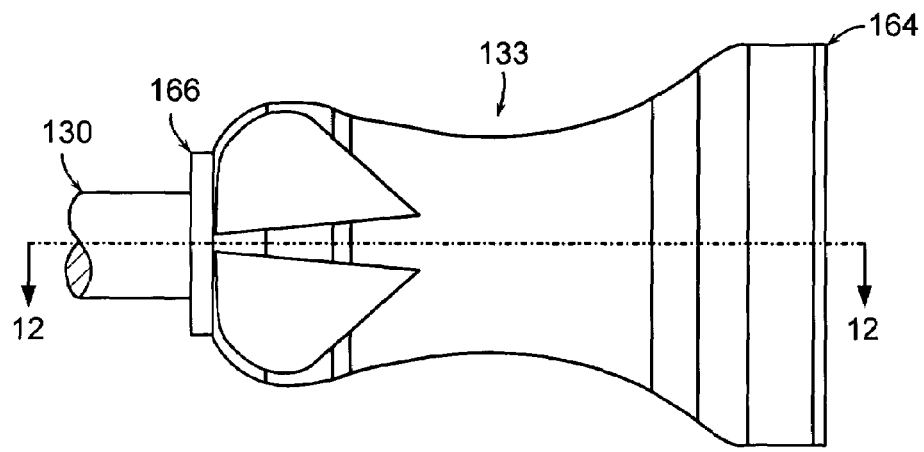
FIG. 12 depicts a schematic side view of the access sheath hub of the balloon dilator access sheath assembly of FIG. 4.

The present invention relates to a dilator having an expandable member. The dilator can be used with an access sheath in various surgical procedures requiring access, through, for example, a vessel in the body. Ureteroscopy procedures are a non-limiting example of such procedures. Other procedures include an endopyelotomy procedure to treat a uretero-pelvic junction obstruction, the treatment of urethral strictures, percutaneous renal surgery, and vascular access surgery.

In an ureteroscopy procedure, a guide wire is introduced into the urethra. The wire then is fed through the urinary tract into the bladder. From the bladder, the wire passes through the ureteral orifice and into the ureter. If access to the kidney is required, the wire is fed through the ureter, to the kidney, where its distal end can be lodged.

In current ureteroscopy procedures, after introducing the guide wire, a medical professional has several choices. In a first method, the medical professional can introduce a dilating element that is connected to a surrounding sheath over the guide wire. As the dilating element is introduced over the guide wire, the dilating element radially expands the tissue of the urinary tract. After the dilator with the connected surrounding sheath has been guided to its required destination, the dilating element is detached from the sheath and removed from the lumen of the sheath, leaving the sheath in place. In a second method, after the guide wire is introduced, a medical professional can slide a sheath that also functions as a dilating element over the length of the guide wire. This type of device generally has a tapered tip to gradually dilate tissue.

Medical professionals performing ureteroscopy procedures sometimes encounter difficulties gaining access to various parts of the urinary tract because of a blockage of the urinary tract, for example, but without limitation, a constriction of the ureteral orifice, which is situated between the bladder and the ureter, a stricture, a stone, or a tumor. If the first method, as described above, is used to access the ureter, it may be necessary to use a balloon to expand the tissue of the ureteral orifice to enable the sheath to enter the ureter. This requires, for example, that the medical professional remove the dilating element from the lumen of the sheath and, then, introduce the balloon into the lumen. The balloon is then used to expand the tissue of the ureteral orifice, and then the sheath is advanced through the ureteral orifice. Once the sheath has passed through the ureteral orifice into the ureter, the balloon is removed from the sheath, and other tools, such as the dilating element, are re-introduced into the sheath's lumen to continue the procedure being conducted. Alternatively, if a balloon is not used, the dilating element may be forced through the ureteral orifice, potentially damaging the orifice. If access to the ureteral orifice is not possible, then the patient may have to undergo a more invasive procedure, such as percutaneous access or open surgery. Likewise, if the second method, as described above, is used to access the ureter and a balloon is required to expand the ureteral orifice, the medical professional will need to remove the sheath/dilator device from the patient before inserting a balloon into the patient. Once the blockage has been overcome, the balloon is removed from the body, and the dilator/sheath device is re-inserted into the patient. This method also has the disadvantage that the passage held open by the sheath must be re-established each time the dilator/sheath device is reinserted into the patient.

In addition to being unable to access the ureteral orifice, other problems encountered by medical professionals which hinder the passage of the sheath are the presence of strictures, stones, or tumors in the ureter. In this situation, if the first method of accessing the ureter is used as described above, upon encountering the stricture, stone, or tumor, the dilating element is removed from the sheath, and a balloon is introduced through the lumen of the sheath to expand the passage. Potentially, other tools, such as a lithotriptor or a grasper, may need to be used as well to reduce, remove, or bypass the obstruction. Once the stricture, stone or tumor is relieved or bypassed, the balloon is removed from the sheath, and other tools, such as the dilating element, are re-introduced into the sheath. If the second method as described above is used to access the ureter, and the dilator/sheath device is incapable of bypassing the stricture, stone or tumor, the dilator/sheath device is removed from the body, and a balloon is inserted to expand the passage. Once the stricture, stone or tumor is bypassed, the balloon is removed from the body, and the dilator/sheath device is re-introduced.

Accordingly, dilators of the invention have the functionality of both a dilating element and an expandable member, such as a balloon, in the same device. One advantage of combining these functions in a single device is that a medical professional does not have to remove a dilator from a sheath before inserting an expandable member in order to, for example, remove a blockage. This reduces the time of surgery to the benefit of the patient, and simplifies the surgical procedure for the benefit of the medical professional. Moreover, costs are reduced, because the need for a separate dilator and an expandable member is avoided. Furthermore, when the dilator having an expandable member is used with an access sheath, additional benefits are realized. For instance, the access sheath protects tissue from damage when tools and instruments, such as lasers, graspers, lithotriptors, scopes, and dilators according to the invention are passed through the lumen of the access sheath, which reduces healing time for the patient. The access sheath also improves irrigation, which can enhance visibility for the medical professional.

Now, referring to FIGS. 1 and 2, a balloon dilator access sheath assembly 2 according to the invention includes a dilator 4 having a proximal end 6 and a distal end 8 (As used herein, "proximal" refers to the end of the device closest to a medical professional during use of the device and "distal" refers to the end of the device furthest from the medical professional during use). A wall 21 of the dilator 4 defines a lumen therethrough 10. Alternatively, the dilator can be solid and utilized without a guide wire. The balloon dilator access sheath assembly 2 also includes an access sheath 30 which is coaxial with and surrounds the dilator 4, when assembled. The dilator 4 is sufficiently rigid along its length to perform its dilation function. Such rigidity typically is greater than expansion devices, including balloon expanders, used in the art. This allows the dilator 4 to dilate tissue without buckling. For example, the dilator can be made from a material having a durometer value of about 40 to about 80 on a Shore A scale, about 45 to about 75 on a Shore A scale, about 50 to about 70 on a Shore A scale, or about 55 to about 65 on a Shore A scale. These durometers are sufficiently hard so that the dilator is sufficiently rigid to dilate tissue in a body vessel. The thickness of the wall of the dilator also can be varied to create sufficient rigidity, and/or reinforcing materials can be used. Further examples of rigidity are discussed below. The dilator can be manufactured using an extrusion process and can be made from, for example, but without limitation, polyethylene, such as polyethylene having a molecular weight in the range of 50,000 to 100,000; nylon, such as nylon 12, nylon 4-6, and nylon 6-6; Pebax (polyether block amides), for example having a durometer value of about 72 to about 85 on a Shore D scale; polyurethane, for example having a durometer value of about 75 on a Shore D scale; polytetrafluoroethylene (PTFE), particularly fluorinated ethylene propylene (FEP) copolymers; and polyethylene impregnated with PTFE. In certain embodiments, the dilator is made from materials with a flex modulus of about 300 to about 500 MPa.

The external surface of the dilator can have a hydrophilic coating or a silicone coating to ease the passage of the dilator in tissue. Such a hydrophilic coating can be, for example, but without limitation, N-Vinyl Pyrrolidone, Poly Vinyl Alcohol, and Poly Vinyl Pyrrolidone. The hydrophilic coating can be accomplished by coating a device with a primer, such as Bayhydrol 110 (an anionic dispersion of an aliphatic polyester urethane resin in water/n-methyl-2-pyrrolidone) and then bonding a primary layer over the primer. The primary layer can be, without limitation, an acrylamide or a polyurethane-based acrylamide. Alliphatic polyether and polyester polyurethanes also can be used as lubricous coatings.

Located at the proximal end 6 of the dilator 4 is a hub 12. The hub 12, in this embodiment, is a bi-furcated hub. Located near the distal end 8 of the dilator 4 is an expandable member 14. The expandable member 14 surrounds the dilator 4 and is coaxial with the dilator 4. In this embodiment, the expandable member 14 is a low profile, high-pressure balloon. The balloon can be compliant or non-compliant and can be made from, for example, but without limitation, nylon, polyethylene terephthalate (PET), polyethylene, polyurethane, Pebax, silicone, or latex. Alternatively, the expandable member can be, for example, several balloons, expandable metal elements, sequential fascial PTFE dilators, single step fascial PTFE dilators, an inverse Chinese finger, cutting balloons, or a braided cage.

The expandable member 14 is connected to the dilator 4. The connection can be accomplished by bonding balloon necks 16, which are coaxial with the dilator 4, to the outer surface of the dilator 4. The balloon necks 16 have substantially the same inner diameter as the outer diameter of the dilator 4. Such an expandable member can be formed through a blow molding process and then can be fitted over the dilator. Briefly, in the blow molding process, a section of tubing is expanded about its middle section, leaving the ends (i.e., the balloon necks 16) unexpanded. The section of tubing then is slid over the dilator to its proper position, and the balloon necks are connected to the dilator. Connection can be accomplished through the use of an adhesive bond, through the use of a shrink fit bond, through the use of an RF bond, through the use of an ultrasonic bond, through the use of a laser bond, or through the use of an interference fit.

The distal end 8 of the dilator 4 has a tapered tip 18. The tapered tip 18 is integral with the dilator 4. Alternatively, the tapered tip can be a separate part that is designed to mate with the dilator using any technique known in the art, such as, but without limitation, a press fit, a snap fit, or threading.

When the balloon dilator access sheath assembly 2 is assembled, the access sheath 30, having a circular cross section, is coaxial with and surrounds the dilator 4. Alternatively, the access sheath (and/or dilator) can have an oval cross section. The access sheath 30 has a proximal end 32 and a distal end 34 defining a length therebetween. Generally, the access sheath 30 is less rigid than dilator 4, but sufficiently rigid to avoid buckling, and may be formed using an extrusion process. For example, the access sheath 30 can be made from a material having a durometer value of about 30 to about 50 on a Shore A scale or about 35 to about 45 on a Shore A scale. The wall of the access sheath 30 can also be varied in thickness to vary rigidity, and/or reinforcing materials can be used. Further examples of rigidity are discussed below. To reduce friction when the access sheath 30 is introduced into the body, the access sheath 30 can have a hydrophilic coating, such as those described above. Additionally, the access sheath 30 can be coated or be formed integrally with one or more agents to provide, for example, an anti-inflammatory, analgesic, anti-spasmodic, or anti-microbial effect, alone or in combination, when inserting or upon insertion of the access sheath. Other types of agents are contemplated within the scope of invention for use as a coating on the access sheath or within the access sheath to provide a therapeutic or healing effect. For example, but without limitation, Toradol (ketorolac tromethamine), or Ditropan (oxybutynin chloride), may be incorporated on or into the access sheath to aid healing of urinary tract tissue or to relieve discomfort.

The access sheath can be manufactured from one layer of material or from multiple overlaid or fused layers of the same or different materials, and may or may not include a reinforcing member to increase column strength. For example, an inner surface of the access sheath can comprise, for example, PTFE, or, as another example, Pebax. The reinforcing member can be a stainless steel coil, and the outer surface can comprise, for example, Pebax, or, as another example, Hytrel (a polyether ester elastomer block copolymer consisting of a hard crystalline segment of polybutylene terephthalate and soft amorphous segments based on long-chain polyether glycols). In some cases, a tie layer exists between the inner PTFE surface and the outer Pebax or Hytrel surface. When Pebax is used as an inner or outer surface, Pebax having a durometer value of about 45 to about 72 on a Shore D scale can be used. The access sheath also can be made from polyurethanes having a durometer value of about 45 to about 72 on a shore D scale, nylons, or PTFE impregnated with either Pebax or nylons.

When the access sheath 30 and the dilator 4 are in use, the distal end 34 of the access sheath 30 is spaced apart from the expandable member 14. Alternatively, the distal end of the access sheath can partially or fully cover the expandable member.

The access sheath 30 is connected to a hub 33 at its proximal end 32. In use, the hub 12 of the dilator 4 is received within the hub 33 of the access sheath 30, and the hubs 12, 33 connect. In certain embodiments, the hubs 12, 33 can connect through the use of a friction fit, snap-fit or a compression fit, or by locking, or twisting. During use, the hub 33 of the access sheath 30 holds the hub 12 of the dilator 4 securely in place, such that movement of the dilator 4 relative to the access sheath 30 is minimal or non-existent. Once use of the dilator 4 is no longer required, the dilator 4 can be disconnected and removed from the access sheath 30, leaving the access sheath 30 in place.

FIG. 2 is a cross section of the balloon dilator access sheath assembly 2 taken along line 1-1 in FIG. 1. The dilator 4 has a wall 21 defining a lumen 10. The wall 21 includes an inner wall 20 and an outer wall 22 defining a solid area 24 therebetween. Within the solid area 24, there is a passage 26 that extends from the expandable member 14 towards the proximal end 6 of the dilator 4. At its distal end, the passage 26 communicates with the expandable member 14. An aperture, for example, through the outer wall 22 of the dilator 4 allows communication between the passage 26 and the interior of the expandable member 14. At its proximal end, the passage 26 is accessible to the medical professional through a balloon luer 39.

The expandable member 14 can be inflated by a medical professional by introducing a gas or a liquid, for example, a saline solution, a saline solution mixed with a radioactive isotope, which is useful in radiation treatment, or a saline solution mixed with radiopaque material, into the passage 26 at its proximal end through the balloon luer 39. A syringe can be used to introduce liquid into the passage 26 via the balloon luer 39, or, if a gas is used, an inflator can be used to introduce a controlled volume of gas into the passage 26 through the balloon luer 39. The gas or liquid then travels along the length of the passage 26 to the passage's distal end. Because the expandable member 14 and the distal end of the passage 26 are in communication, when the gas or liquid arrives at the distal portion of the passage 26, the gas or liquid enters the interior of the expandable member 14 through, for example, the aperture between the passage 26 and the expandable member 14. The buildup of pressure within the expandable member 14 causes the expandable member 14 to expand. The medical professional can control the amount of expansion by controlling the amount of liquid or gas introduced into the passage 26, for example, by using a syringe or inflator that includes a pressure gauge. Likewise, to deflate the expandable member 14, the medical professional can remove fluid or gas from the passage 26 and/or the expandable member 14 through the balloon luer 39. This causes a reduction in pressure within the passage 26 and/or expandable member 14 and allows the expandable member 14 to deflate. As a general principle, the medical professional applies a force to the expandable member 14 through the passage 26, expanding the expandable member. To deflate the expandable member, the medical professional removes the force.

In another embodiment, the dilator can have two or more separate lumens. One of the lumens communicates with the expandable member through an aperture in the wall of the dilator. In some embodiments, this lumen ends immediately distal to the aperture, which is proximal to the distal end of the dilator. This lumen also can be smaller than the other lumens. Alternatively, more than one lumen of the dilator communicates with the expandable member. A force is applied to expand the expandable member, for example, using a gas or a liquid, as described above.

Now referring to FIG. 3, in an ureteroscopy procedure according to the invention, the patient can be given local or general anesthetic. A guide wire then is introduced into the urethra 50 and is fed through the bladder 52, ureteral orifice 54, and ureter 56 to the kidney 58. The proximal end of the guide wire then is introduced into the tip 18 of the balloon dilator access sheath assembly 2 such that the balloon dilator access sheath assembly 2 slides over the guide wire. The tip 18 of the dilator 4 is advanced to the orifice of the urethra. As the tip 18 of the dilator 4 moves along the urethra 50, it applies radial pressure to the tissue of the urinary tract, gradually dilating such tissue. Gradual dilation reduces trauma to the patient. The tapered tip 18 of the dilator 4 facilitates, in part, such gradual dilation. Dilating the urinary tract allows the access sheath 30 of the balloon dilator access sheath assembly 2 to be inserted into the body.

Once the balloon dilator access sheath assembly 2 reaches the ureteral orifice 54, the balloon dilator access sheath assembly 2 must be guided through the ureteral orifice 54, which can be difficult. Sometimes, the orifice is constricted, and the expandable member 14 is used to open the ureteral orifice 54. The medical professional expands the expandable member 14, opening the ureteral orifice 54, which allows access to the ureter 56. The expandable member 14 is then deflated, and the balloon dilator access sheath assembly 2 is advanced into the ureter 56. As can be seen, this procedure and device allows the medical professional to utilize both the dilating and expansion functionality of the dilator 4. Moreover, the medical professional does not need to remove the dilator 4 or the entire balloon dilator access sheath assembly 2 to replace it with a separate expandable member.

Alternatively, or in addition, use of the balloon dilator access sheath assembly 2 may be required should a stone, tumor, or stricture be encountered in the ureter. Again, in the same manner described above, the medical professional would expand the expandable member 14 to bypass the obstruction, and then the expandable member 14 would be contracted. The balloon dilator access sheath assembly 2 would then be further guided to its required destination. Once the balloon dilator access sheath assembly 2 is located at the desired location, the dilator 4 is disconnected from the access sheath 30 and removed from the lumen of the access sheath 30, thereby allowing other tools to be inserted into the lumen.

In addition to the uses described above, the expandable member 14 can be used as a placement guide. In this use, the tip 18 of the dilator 4 is guided through the ureter 56, to the renal pelvis of the kidney. At the renal pelvis, the expandable member 14 is inflated. The medical professional then gently pulls the balloon dilator access sheath assembly 2 proximally, such that expandable member 14 lodges in the renal pelvis. Lodging of the expandable member 14 in the renal pelvis indicates to the medical professional that the balloon dilator access sheath assembly 2 is properly placed. Once the balloon dilator access sheath assembly 2 is properly placed, the expandable member 14 is deflated, and the dilator 4 is removed from the lumen of the access sheath 30.

Now, referring to FIGS. 4 and 5, an embodiment of the invention is illustrated, with reference to dimensions of the dilator and access sheath which may be particularly suited to application of the balloon dilator access sheath assembly in a ureteroscopy application. This embodiment may be used by a medical professional in the same manner as described above for the embodiment shown in FIGS. 1-3. The dimensions here are not intended to be restrictive, but are merely illustrative of one embodiment of the invention. In this embodiment, the balloon dilator access sheath assembly 102 includes a dilator 104 having a proximal end 106 and a distal end 108 defining a length H therebetween. The length H of the dilator can range from approximately 12.065 inches to approximately 19.288 inches. The wall of the dilator 104 defines a lumen 100 therethrough. The balloon dilator access sheath assembly 102 also includes an access sheath 130 that is coaxial with and surrounds the dilator 104. The dilator can be manufactured using an extrusion process and can be made from a mixture of low density polyethylene, with approximately 20% barium sulfate. Alternatively, the dilator can be made from the materials described above in the first embodiment shown in FIGS. 1-3 and can also have a hydrophilic coating. The dilator 104 is sufficiently rigid along its length to perform its dilation function without buckling. For example, the dilator 104 can be made from a material having a durometer value of about 40 to about 80 on a Shore A scale, about 45 to about 75 on a Shore A scale, about 50 to about 70 on a Shore A scale, or about 55 to about 65 on a Shore A scale. These durometers are sufficiently hard so that the dilator 104 is sufficiently rigid to dilate tissue in a body vessel. The thickness of the wall of the dilator 104 also can be varied to create sufficient rigidity, and/or reinforcing materials can be used. Further examples of rigidity are discussed below.

The proximal end 106 of the dilator 104 is connected to a hub 112, which is designed to fit in a bore 168 of a hub 133 of the access sheath 130. Located near the distal end 108 of the dilator 104 is an expandable member 114 (a balloon), which surrounds the dilator 104 and is coaxial with the dilator 104. The expandable member 114 can have any of the features described in the embodiment shown in FIGS. 1-3, and can be constructed and connected to the dilator using any technique previously described.

The dilator 104 has a wall which defines a solid area between its inner and outer diameters. Within the solid area, there is a passage that extends longitudinally from the expandable member 114 towards the proximal end 106 of the dilator 104. At its distal end, the passage communicates with the expandable member 114. An aperture, for example, through the wall of the dilator 104 allows communication between the passage and the interior of the expandable member 114. At its proximal end, the passage is accessible to the medical professional, allowing the expandable member 114 to be inflated and deflated as described in the embodiment shown in FIGS. 1-3.

Still referring to FIGS. 4 and 5, the distal end 108 of the dilator 104 also has a tapered tip 118. The tapered tip 118 is integral with the dilator 104. In certain circumstances, the tapered tip 118 can have a length J of 0.755 inches and an exposed tip length K of 1.11 inches. The tapered tip 118 can have at its distal most end an inner diameter D of 0.042 inches and an outer diameter E of 0.066 inches. In these circumstances, proximal to the tapered tip 118, the dilator's 104 outer diameter F can be 0.142 inches and its inner diameter G can be 0.98 inches, the sheath tip inner diameter B can be 0.139 inches, and the sheath outer diameter C can be 0.172 inches. In other circumstances, the tapered tip 118 can have a length J of 0.895 inches and at its distal end 108 can have an inner diameter D of 0.042 inches and an outer diameter E of 0.066 inches. In these circumstances, proximal to the tapered tip 118, the dilator 104 can have an outer diameter F of 0.170 inches and an inner diameter G of 0.122 inches, the sheath tip inner diameter B can be 0.167 inches, and the sheath outer diameter C can be 0.200 inches. In this circumstance, the exposed tip length K of the dilator 104 can be 2.807 inches.

When the assembly 102 is assembled, the access sheath 130, having a circular cross section, is coaxial with and surrounds the dilator 104. The access sheath 130 has a proximal end 132 and a distal end 134 defining a length A therebetween. In this embodiment, the distal end 134 of the access sheath 130 ends proximal to the distal end 108 of the dilator 104, such that there is an exposed tip length K of the dilator 104 that is not surrounded by the access sheath 130. The access sheath 130 can have a sheath working length A ranging from about 10.0 to 19.0 inches.

The access sheath 130 is less rigid than dilator 104, but sufficiently rigid to avoid buckling. For example, the access sheath 130 can be made from a material having a durometer value of about 30 to about 50 on a Shore A scale or about 35 to about 45 on a Shore A scale. The wall of the access sheath 130 can also be varied in thickness to vary rigidity, and/or reinforcing materials can be used. Further examples of rigidity are discussed below. In this embodiment, the access sheath 130 comprises a reinforcing member incorporated into the wall of the access sheath 130. The outer surface layer of the access sheath 130 can be made from Pebax, and the inner surface layer of the access sheath 130 can be made from PTFE. Alternatively, any materials described in the embodiment in FIGS. 1-3 for the construction of the access sheath can be used in this embodiment. The reinforcing member incorporated in the access sheath 130 is a rolled flat wire spring, which increases the column strength of the access sheath 130. Further, the access sheath can be coated or manufactured to include, for example, but without limitation to, one or more agents, such as Toradol, as described above with respect to the embodiment in FIGS. 1-3.

Turning now to FIGS. 6, 7, 8 and 9, the hub 112 of the dilator 104 according to this embodiment is shown in greater detail. The hub 112 is made from Delrin (an acetal homopolymer), using an injection molding process. The hub 112 defines a generally cylindrical bore 150 which extends longitudinally through the hub 112 from a distal end 151 of the hub 112 to a proximal end 152. In this embodiment, the hub 112 and the dilator 104 are created as an integral device using injection molding manufacturing. Alternatively, if the parts are made separately, the dilator 104 can be received in the bore 150 of the hub 112 at the distal end 151 of the hub 112, and connected to the hub 112 using any technique known in the art, for example, threading or by the use of an adhesive. Located at the proximal end 152 of the hub 112 is a luer lock fitting 155 which is integral with the hub 112. Alternatively, the luer lock fitting can be a separate part that is connected to the hub using, for example, but without limitation, an adhesive bond, or by threading. In use, the luer lock fitting 155 provides a means for the medical professional to attach other medical equipment, such as a drainage tube, to the hub 112 of the dilator 104. Alternatively, during use, a contrasting fluid can be injected through the luer lock fitting 155 to aid the medical professional in the procedure being conducted. The hub 112 also includes a tab 156 on its bottom portion. Located on the tab 156 is a protrusion 157 which allows the hub 112 of the dilator to snap fit into the hub 133 of the access sheath 130. Located at the top portion of the dilator hub 112, is a semicircular flange 159 which abuts the proximal end 164 of the hub 133 of the access sheath 130 when the hub 112 of the dilator 104 is connected to the hub 133. The flange 159 prevents the hub 112 from sliding distally when the dilator 104 is in the lumen of the access sheath 130. In this embodiment, the length L of the hub 112 can be made to measure, so that the hub 112 of the dilator 104 can be received in the bore 168 of the hub 133 of the access sheath 130.

Figure 13:
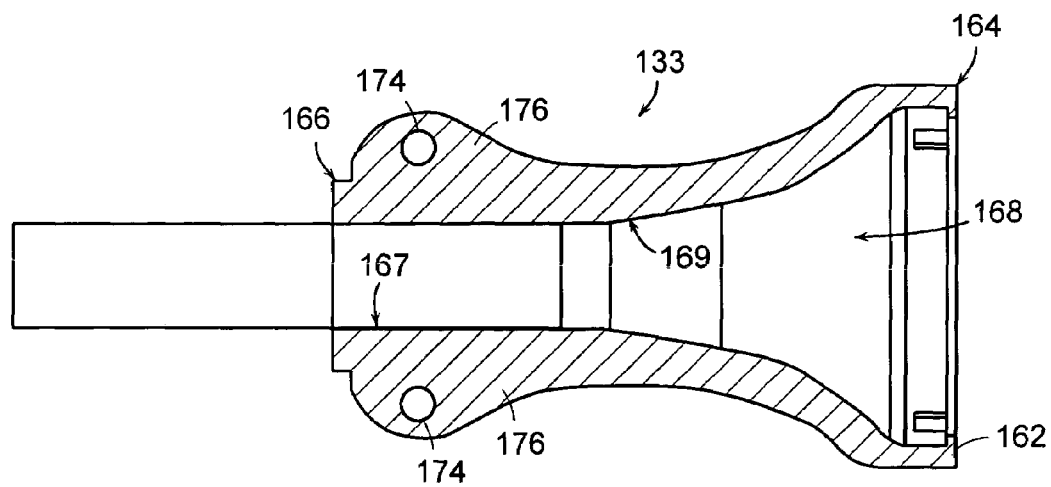
FIG. 13 depicts a schematic cross section view of the access sheath hub of FIG. 12 taken along line 12-12 of FIG. 12.
Figure 14:
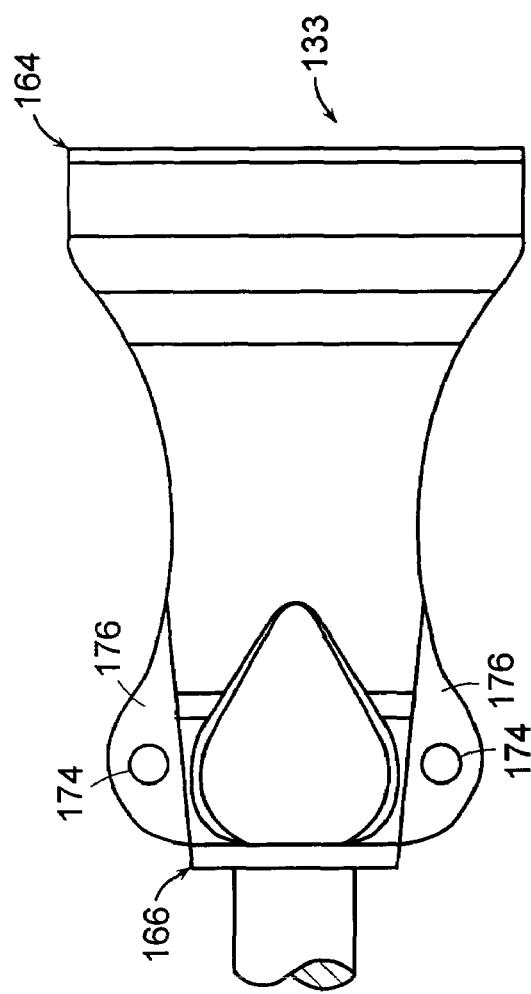
FIG. 14 depicts a schematic side view of the access sheath hub of FIG. 12 rotated 90 degrees about its longitudinal axis.

Turning to FIGS. 10 through 15, the hub 133 of the access sheath 130 is shown in greater detail. The hub 133 is generally tubular in shape and has a proximal end 164 and a distal end 166. In this embodiment, the hub 133 can have a length L1 of approximately 1.17 inches, and can be made from Pebax in an injection molding process. The interior of the hub 133 defines a bore 168. The bore 168 is widest at the proximal end 164 of the hub 133 and gradually tapers towards the distal end 166 of the hub 133, into a generally cylindrical portion 167. The generally cylindrical portion 167 has a diameter that is approximately equivalent to the outer diameter of the access sheath 130. In this embodiment, the access sheath 130 is injection molded with the hub 133 to create an integral device. Alternatively, the hub 133 and the access sheath 130 can be made as separate parts. In this circumstance, the access sheath 130 can be connected to the hub 133 by sliding the access sheath 130 into the hub 133 at its distal end 166. The access sheath 130 is then connected to the inner wall 169 of the bore 168 along its generally cylindrical portion 167 using any technique known in the art, such as adhesive bonding or threading. At the proximal end 164 of the hub 133, the bore 168 of the hub 133 has an orifice 170 through which the hub 112 of the dilator 104 can be received. The orifice 170 can, for example, have a diameter D1 of 0.595 inches. Also at the proximal end 164 of the hub 133 is a locking mechanism 162, which extends slightly radially into the bore 168 of the hub 133. In use the locking mechanism 162 receives the protrusion 157 of the tab 156 of the hub 112 of the dilator 104, which connects the hub 112 of the dilator 104 to the hub 133 of the access sheath 130. Referring to FIG. 13, the hub 133 of the access sheath 130 also includes a pair of through holes 174 located on a portion 176. In use, the through holes 174 on the portion 176 can be used to suture the hub 133 of the access sheath 130 to surgical drapes.

Figure 15:
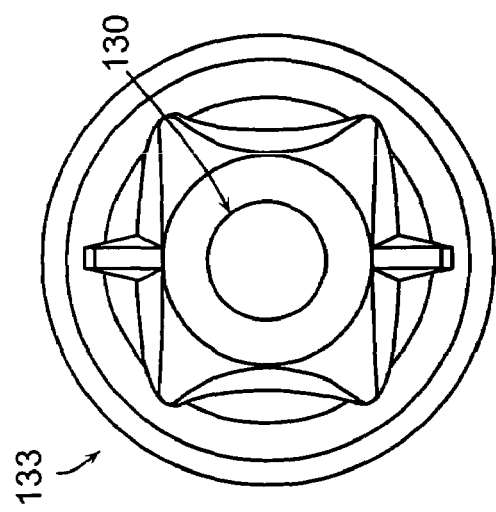
FIG. 15 represents a schematic distal end view of the access sheath hub of FIG. 14.
Figure 15A:
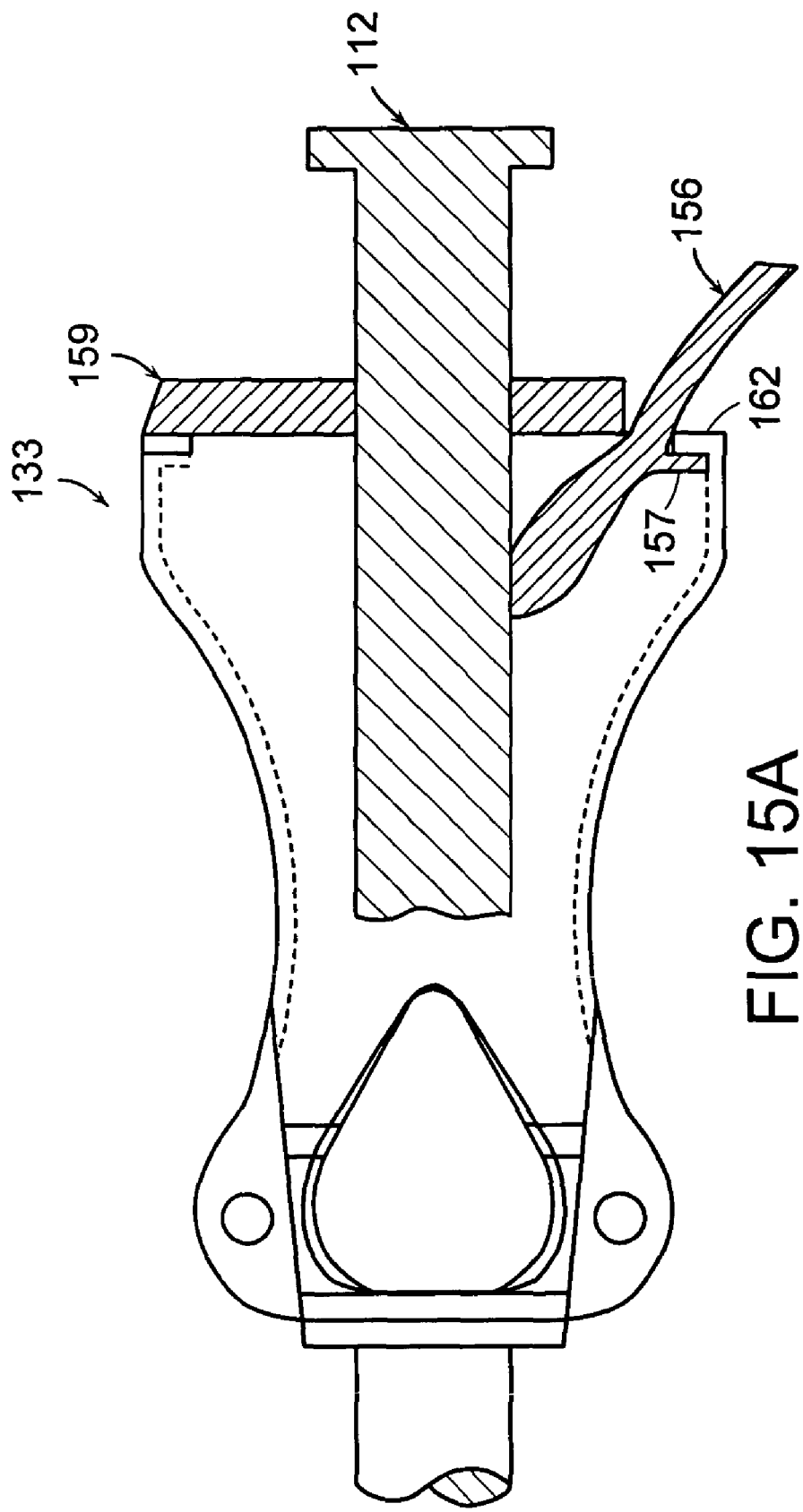
FIG. 15A depicts a schematic cross section view of the dilator hub of the balloon dilator access sheath assembly of FIG. 4 connected to the access sheath hub of the same assembly.

In use, as shown in FIG. 15A, the hub 112 of the dilator 104 is received by the hub 133 of the access sheath 130, and the hubs 112, 133 connect. The connection between the hubs 112, 133 is tight, minimizing or eliminating altogether the relative movement between the dilator 104 and the access sheath 130. More specifically, to insert the hub 112 of the dilator 104 into the access sheath hub 133, a medical professional introduces the tip 118 of the dilator 104 into the bore 168 of the hub 133 of the access sheath 130, and gradually slides the dilator 104 distally into the access sheath 130. To place the hub 112 of the dilator 104 into the bore 168 of the hub 133, the medical professional squeezes the tab 156 of the hub 112 slightly upwardly, and slides the hub 112 of the dilator 104 into the bore 168 of the hub 133 of the access sheath 130 until the flange 159 abuts the distal end 164 of the hub 133. When the flange 159 abuts the distal end 164 of the hub 133, the medical professional releases the tab 156 and the protrusion 157 on the tab 156 snaps into the locking mechanism 162, preventing the hub 112 from sliding proximally out of the hub 133.

Once use of the dilator 104 is no longer required, the dilator 104 can be disconnected, and removed from the access sheath 130, leaving the access sheath 130 in place. To remove the dilator 104, the medical professional squeezes the tab 156 of the hub 112 of the dilator 104, and slides the hub 112 of the dilator 104 slightly distally to release the protrusion 157 from the locking mechanism 162. The hub 112 of the dilator 104 can then be slid proximally, thereby removing the hub 112, and eventually the dilator 104, from the hub 133 of the access sheath 130.

Referring to FIG. 16, the balloon dilator access sheath assembly 102 can be created in several different size configurations. The dimensions here are not intended to be restrictive, but are merely illustrative of exemplary embodiments of the invention. Unless otherwise noted, the dimensions in FIG. 16 are in inches. The notation "O.D." refers to outer diameter, and the notation "I.D." refers to inner diameter. Each row of FIG. 16 contains a different aspect of the device. For example, the device shown in row 1 has a sheath working length A of 10.94 inches, with a sheath tip inner diameter B of 0.139 inches, a sheath outer diameter C of 0.172 inches, a dilator tip inner diameter D of 0.042 inches, a dilator tip outer diameter E of 0.066 inches, a dilator body outer diameter F of 0.142 inches, a dilator body inner diameter G of 0.098 inches, and a dilator working length H of 12.065 inches. The length J of the tapered portion of the dilator tip 118 is 0.755 inches, and the exposed tip length K of the dilator 104 is 1.11 inches.

As described above, a dilator according to the invention and/or a balloon dilator access sheath assembly according to the invention can have sufficient rigidity to dilate tissue in a body vessel. Referring to FIGS. 17 and 18, when the balloon dilator access sheath assembly (or a dilator according to the invention) is tested for rigidity, a three point bend stiffness test can be utilized. The purpose of the three point bend stiffness test is to measure the force required for a push rod to travel a certain distance when the push rod pushes on the balloon dilator access sheath assembly, thereby bending the balloon dilator access sheath assembly. In the test, the balloon dilator access sheath assembly is supported by a pair of holders spaced two inches apart. A push rod having a radius of 0.159 inches is then used to apply a force to the midpoint of the supported section of the balloon dilator access sheath assembly such that the force applied is sufficient to move the push rod a reference distance of 0.375 inches. All of the tests are conducted at ambient conditions. The force measurements in FIGS. 17 and 18 are given in pounds-force (lbf) while the dimensions are given in inches. The notation "O.D." refers to outer diameter, and the notation "I.D." refers to inner diameter.

The rigidity measurements in FIG. 17 indicate that the tested balloon dilator access sheath assemblies, such as those described above, have sufficient rigidity to dilate tissue in a body vessel. The force measurements here are not intended to be restrictive, but are merely illustrative of exemplary embodiments of the invention. In FIG. 17, assemblies having a dilator with an 11 French outer diameter and an access sheath with a 13 French outer diameter were tested. Three different sized dilators, each having a different sized inner diameter, were used with the same sized access sheath. The inner diameters of the dilators tested were 0.098 inches, 0.082 inches, and 0.060 inches. Each row of FIG. 17 contains a different sample of the assembly that was tested. For example, the first sample was three assemblies. The first assembly tested included a dilator having an inner diameter of 0.098 inches, and a force of 1.39 lbf was required to move the push rod the reference distance. The second assembly tested included a dilator with an inner diameter of 0.082 inches, and a force of 1.62 lbf was required to move the rod the reference distance. The third assembly tested included a dilator with an inner diameter of 0.060 inches, and a force of 1.75 lbf was required to move the push rod the reference distance. The bottom rows of FIG. 17 show the average force, minimum force, and maximum force required to move the push rod the reference distance for each of the six assembly samples tested for each of the three different dilator inner diameter sizes. For example, when a dilator with an inner diameter of 0.098 inches was tested, the average force across the six assembly samples required to move the push rod the reference distance was 1.49 lbf, the maximum force was 1.67 lbf, and the minimum force was 1.25 lbf.

In FIG. 18, assemblies having a dilator with a 13 French outer diameter and an access sheath with a 15 French outer diameter were tested. Three different sized dilators, each having a different sized inner diameter, were used with the same sized access sheath. The inner diameters of the dilators tested were 0.122 inches, 0.090 inches, and 0.110 inches. Each row of FIG. 18 contains a different sample of the assembly that was tested. For example, the first sample was three assemblies. The first assembly tested included a dilator having an inner diameter of 0.122 inches, and a force of 1.60 lbf was required to move the push rod the reference distance. The second assembly tested included a dilator with an inner diameter of 0.090 inches, and a force of 2.02 lbf was required to move the rod the reference distance. The third assembly tested included a dilator with an inner diameter of 0.110 inches, and a force of 1.80 lbf was required to move the push rod the reference distance. The bottom rows of FIG. 18 show the average force, minimum force, and maximum force required to move the push rod the reference distance for each of the six assembly samples tested for each of the three different dilator inner diameter sizes. For example, when a dilator with an inner diameter of 0.122 inches was tested, the average force across the six assembly samples required to move the push rod the reference distance was 1.73 lbf, the maximum force was 1.83 lbf, and the minimum force was 1.60 lbf.

While the invention has been shown and described with reference to specific embodiments, it should be understood by those skilled in the art that various changes in form and detail may be made therein without departing from the spirit and scope of the invention. It should be further reiterated that this device is not limited to use in ureteroscopy procedures, but can also be used to access other vessels and orifices of the body.

What is claimed is:

1. An apparatus, comprising:
a flexible sheath having a proximal end portion and a distal end portion, the flexible sheath having a hub at the proximal end portion, the flexible sheath defining an opening at the proximal end portion, an opening at the distal end portion and a lumen therethrough, the flexible sheath configured to be inserted into a body of a patient; and
a dilator disposed within the lumen of the flexible sheath such that the dilator extends through the opening at the distal end portion of the flexible sheath and the opening at the proximal end portion of the flexible sheath, the dilator including a tapered portion configured to dilate tissue within the body of the patient and an expandable portion configured to expand outwardly from the dilator, the dilator having a hub including a flange and a tab, the tab having a fixed end coupled to the hub of the dilator, the tab having a free end, the tab having a protrusion extending substantially perpendicular to a longitudinal axis of the dilator disposed between the fixed end and the free end,
the dilator being configured such that distal and proximal movement of the dilator relative to the flexible sheath is limited when the hub of the dilator is positioned such that the protrusion of the tab is configured to engage a ridge extending inwardly from an internal surface of the hub of the flexible sheath and the flange is configured to engage an outside surface of the ridge of the flexible sheath, the free end of the tab being disposed outside the hub of the flexible sheath when the protrusion is situated to engage the ridge of the internal surface of the hub of the flexible sheath.

2. The apparatus of claim 1, wherein a proximal end portion of the dilator is removably coupled to the proximal end portion of the flexible sheath.

3. The apparatus of claim 1, wherein the first hub is configured to be removably coupled to the second hub.

4. The apparatus of claim 1, wherein:
the second hub includes an inner receiving portion, the inner receiving portion including the ridge and being a portion of the lumen and being configured to receive and engage the protrusion such that the first hub can be lockably coupled to the second hub via the protrusion to resist distal and proximal movement of the dilator relative to the flexible sheath.

5. The apparatus of claim 1, wherein the dilator defines a lumen therethrough, the lumen configured to receive a portion of a guide wire.

6. The apparatus of claim 1, wherein the dilator defines a lumen therethrough, the lumen configured to supply a fluid to the expandable portion.

7. The apparatus of claim 1, wherein the expandable portion of the dilator is disposed outside of the lumen defined by the flexible sheath.

8. The apparatus of claim 1, wherein the dilator is constructed from a material having a durometer value of between 40 and 80 on the Shore A scale.

9. The apparatus of claim 1, wherein an outer surface of at least one of the dilator or the flexible sheath includes a hydrophilic coating.

10. The apparatus of claim 1, wherein the expandable member of the dilator is used to place the flexible sheath in a specified location in a ureter.

11. The apparatus of claim 1, wherein the hub of the flexible sheath and the hub of the dilator are lockably coupled to resist proximal movement of the dilator relative to the flexible sheath when the flexible sheath is being placed.

12. The apparatus of claim 1, wherein the such that the tab can be actuated via the free end of the tab when the protrusion is situated to engage the ridge inside the hub of the flexible sheath.

13. The apparatus of claim 1, wherein the tab has a longitudinal axis that is non-parallel to a longitudinal axis of the flexible sheath, and the expandable portion is configured to be expanded to dilate a lumen of a body when the protrusion is situated to engage a surface inside the hub of the flexible sheath.

14. The apparatus of claim 1, wherein the tab is configured to be moved between a first position and a second position such that the hub of the dilator can be coupled to the hub of the flexible sheath, the expandable portion is configured to be expanded when the protrusion is configured to engage the ridge of the hub of the flexible sheath.

15. The apparatus of claim 1, wherein:
the free end of the tab is disposed proximally with respect to the ridge when the protrusion is situated to engage the ridge; and
the fixed end of the tab is disposed distally with respect to the ridge when the protrusion is situated to engage the ridge.

16. An apparatus, comprising:
a flexible sheath having a proximal end portion and a distal end portion, the flexible sheath defining an opening at the proximal end portion, an opening at the distal end portion and a lumen therethrough, the flexible sheath configured to be inserted into a body of a patient;

a dilator disposed within the lumen of the flexible sheath such that the dilator extends through the opening at the distal end portion of the flexible sheath and the opening at the proximal end portion of the flexible sheath, the dilator including a tapered portion configured to dilate tissue within the body of the patient and an expandable portion configured to expand outwardly from the dilator;

a first hub coupled to the proximal end portion of the dilator, the first hub including a tab and a flange separate from the tab, the tab having a first end and a second end, the tab being coupled at the first end to the first hub; and a second hub coupled to a proximal end portion of the flexible sheath, the second hub including a receiving portion having a protrusion extending radially inward from an inner sidewall of the receiving portion, the protrusion having an inner surface and an outer surface opposite the inner surface, the receiving portion configured to receive a portion of the tab, the inner surface of the protrusion configured to engage the tab and the outer surface configured to engage the flange such that the first hub can be lockably coupled to the second hub, thereby resisting relative motion between the dilator and the flexible sheath, the second end of the tab is disposed outside the receiving portion when the first hub is lockably coupled to the second hub.

17. The apparatus of claim 16, wherein the tab has a first position, in which the dilator can be moved relative to the flexible sheath, and a second position, in which the first hub is lockably coupled to the second hub.

18. The apparatus of claim 16, wherein the expandable portion of the dilator is disposed outside of the lumen defined by the flexible sheath.

19. The apparatus of claim 16, wherein the dilator defines a lumen therethrough, the lumen configured to receive a portion of a guide wire.

20. The apparatus of claim 16, wherein the dilator defines a lumen therethrough, the lumen configured to supply a fluid to the expandable portion.

21. The apparatus of claim 16, wherein the dilator is constructed from a material having a durometer value of between 40 and 80 on the Shore A scale.

22. The apparatus of claim 16, wherein an outer surface of at least one of the dilator or the flexible sheath includes a hydrophilic coating.

23. The apparatus of claim 16, wherein the dilator and the flexible sheath are lockably coupled using the first hub and the second hub to facilitate placement of the dilator and the flexible sheath in a ureter of a patient.

24. The apparatus of claim 16, wherein the expandable portion of the dilator is used to place the flexible sheath in a specified location in a ureter of a patient.

25. The apparatus of claim 16, wherein the first end of the tab is within the first hub when the first hub is lockably coupled to the second hub, the receiving portion of the second hub is a portion of the lumen, and the first hub has a flange disposed outside of the second hub when the first hub is lockably coupled to the second hub via the tab.

26. The apparatus of claim 16, wherein the tab is configured to be moved between a first position and a second position, the first hub is configured to be lockably coupled to the second hub when the tab is in the second position, the tab is biased towards the second position.

27. The apparatus of claim 16, wherein the tab has a longitudinal axis biased away from to a longitudinal axis of the dilator.

28. The apparatus of claim 16, wherein the first hub is configured to be lockably coupled to the second hub when at least a portion of the first hub is disposed within the second hub in a first position, the first hub is configured to be moved from the first position to a second position disposed outside of the second hub when the tab is actuated and the first hub is moved proximally relative to the second hub.

29. The apparatus of claim 16, wherein the tab is one and only one tab extending radially from the first hub.

* * * * *